(12) United States Patent
Bunyan

(10) Patent No.: US 6,783,512 B2
(45) Date of Patent: Aug. 31, 2004

(54) POWERED APPLICATOR

(75) Inventor: Glenn Walter Bunyan, Pelton (AU)

(73) Assignee: N.J. Phillips PTY. Limited, Somersby (AT)

( * ) Notice: Subject to any disclaimer, the term of this patent is extended or adjusted under 35 U.S.C. 154(b) by 0 days.

(21) Appl. No.: 10/279,376

(22) Filed: Oct. 24, 2002

(65) Prior Publication Data

US 2003/0093033 A1 May 15, 2003

(30) Foreign Application Priority Data

Nov. 12, 2001 (AU) .............................................. PR8804

(51) Int. Cl.$^7$ ................................................ A61M 1/00
(52) U.S. Cl. ...................................... 604/152; 604/192
(58) Field of Search ........................ 604/131, 134–137, 604/151–157, 162, 184, 186, 187, 192, 198, 207, 218, 223, 263, 150

(56) References Cited

U.S. PATENT DOCUMENTS

| | | | |
|---|---|---|---|
| 3,563,098 A | * | 2/1971 | Gley ................................ 74/2 |
| 4,442,836 A | * | 4/1984 | Meinecke et al. ........... 606/182 |
| 4,487,602 A | * | 12/1984 | Christensen et al. ......... 604/137 |
| 4,676,781 A | * | 6/1987 | Phillips et al. ............... 604/135 |
| 4,717,383 A | * | 1/1988 | Phillips et al. ............... 604/135 |
| 4,787,891 A | * | 11/1988 | Levin et al. .................. 604/136 |
| 5,122,119 A | * | 6/1992 | Lucas ........................... 604/138 |
| 5,451,210 A | * | 9/1995 | Kramer et al. ............... 604/137 |
| 5,567,160 A | * | 10/1996 | Massino ....................... 434/262 |
| 6,183,444 B1 | * | 2/2001 | Glines et al. ................. 604/187 |
| 6,565,528 B1 | * | 5/2003 | Mueller ........................ 604/106 |

* cited by examiner

*Primary Examiner*—Brian L. Casler
*Assistant Examiner*—Michael M. Thompson
(74) *Attorney, Agent, or Firm*—Fullbright & Jaworski LLP

(57) ABSTRACT

A power injector 10 that includes a solenoid 23 that moves a piston to cause a liquid to be injected via the needle 13. A shroud 27 engages a switch 28 to cause electric energy to be delivered to the solenoid 24 to cause actuation thereof.

7 Claims, 2 Drawing Sheets

US 6,783,512 B2

POWERED APPLICATOR

TECHNICAL FIELD

The present invention relates to powered applicators such as drenchers, vaccinators, injectors and other fluid dispensing devices, typically used to dispense fluid products such as medicaments and pharmaceuticals to animals,

BACKGROUND OF THE INVENTION

Dispensing of fluid (usually liquid) products (specifically medicaments and pharmaceutical products) has traditionally been achieved utilizing manually powered applicators such as drenchers, vaccinators, injectors and other manual fluid dispensing devices. The limitations of these devices have been the hand pressure required to continually operate such a manual system and the related fatigue and RSI problems resulting from mass usage.

A portable hand held, powered system would alleviate these problems as it would mean that the user would simply need to manually or mechanically press a button or switch which in turn would activate the device delivering the required action under power.

Hand held, portable powered systems currently in use in the pharmaceutical and affiliated fluid dispensing fields are predominantly powered by either compressed air or Liquid Petroleum Gas (LPG). These systems are useful but have limitations in areas/locations where compressed air or high pressure LPG is not readily available. In addition, the most commonly used portable hand held systems in these industries are operated with LPG which can be hazardous when used in confined spaces due to the exhausting of gas into the atmosphere.

OBJECT OF THE INVENTION

It is the object of the present invention to overcome or substantially ameliorate the above disadvantage.

SUMMARY OF THE INVENTION

There is disclosed herein a powered injector to deliver a liquid, said injector including:

a body;

a cylinder in the body;

a piston slidably mounted within the cylinder so as to cooperate therewith to enclose a variable volume chamber;

an outlet extending from said chamber and being adapted to receive a needle through which the liquid is delivered;

a needle shroud movably mounted on the body so as to be movable between an extended position at which the needle would be covered by the shroud, and a retracted position at which the needle is exposed;

an inlet extending to said chamber to deliver liquid thereto;

a solenoid mounted in the body and having a movable actuator connected to the piston, said actuator being caused to move generally linearly from a first position to a second position upon the solenoid being energised, with said piston being caused to reduce die volume of said chamber when said actuator moves from said first position to said second position;

an electric switch connected to said solenoid to deliver electric power thereto to energise said solenoids the switch being mounted on said body so as to be engaged by said shroud when moved to the retracted position thereof; and wherein when said shroud moves to said extended position said electric switch disconnects said solenoid from electric power so that said actuator moves from said second position to said first position causing said piston to increase the volume of said chamber and draw liquid into said chamber via said inlet.

Preferably, said injector includes a spring urging said piston to increase the volume of said chamber.

Preferably, the injector includes a one-way valve in said inlet restricting fluid to flow toward said chamber, and a valve in said outlet restricting fluid to flow toward said needle.

Preferably, said inlet includes a passage extending through said piston and a flexible conduit extending to said passage.

Preferably, a spring urges said shroud to said extended position.

Preferably, said device includes a battery connected to said switch and solenoid.

BRIEF DESCRIPTION OF THE DRAWINGS

A preferred form of the present invention will now be described by way of example e with reference to the accompanying drawings wherein.

DETAILED DESCRIPTION OF THE PREFERRED EMBODIMENTS

Figure 1:
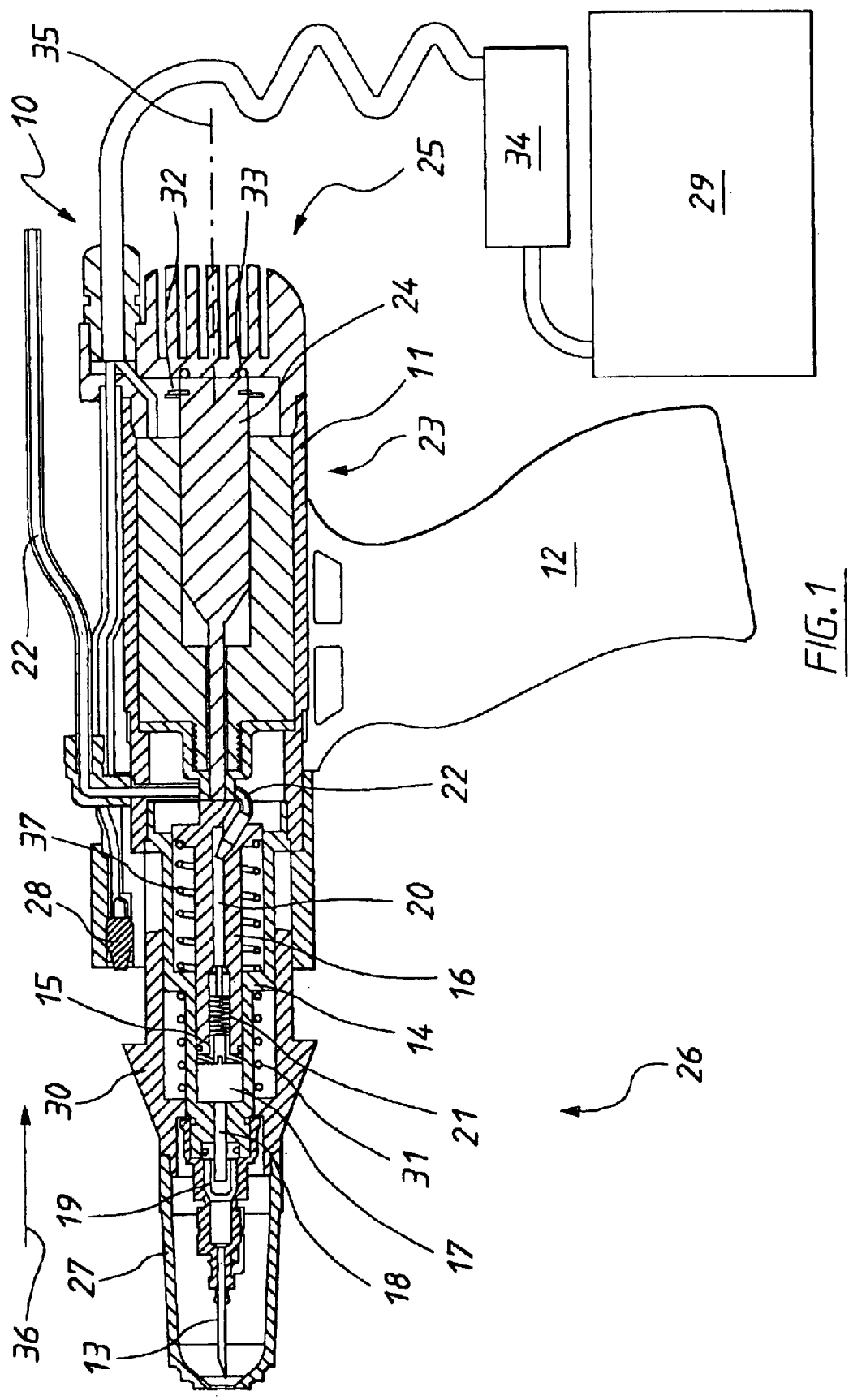
FIG. 1 is a schematic parts section side elevation of an injector in a rest position.

In the accompanying drawings, there is schematically depicted an injector 10 including a body 11 provided with a handle 12. The forward end of the body 11 is provided with an injection needle 13 via which a liquid is delivered.

Mounted within the body 11 is a cylinder member 14 including a cylinder 15. Slidably mounted within the cylinder 15 is a piston 16 which cooperates with the cylinder 15 to enclose a variable volume chamber 17. Extending from the chamber 17 is an outlet 18 communicating with the needle 13. Located within the outlet 18 is a one-way valve 19 that restricts fluid to flow from the chamber 17 to the needle 13.

Extending through the piston 16 is an inlet passage 20 within which there is located a one-way valve 21 restricting fluid to flow through the passage 20 toward the chamber 17. Extending from the passage 20 is a flexible conduit 22 that exits from the body 11 and is connected to a supply of liquid to be delivered. Extending between the cylinder member 14 and piston 16 is a spring 37 that urges the piston 16 to increase the volume of the chamber 17, that is the spring 37 urges the piston 16 toward the rear 25 of the body 11.

Mounted in the rear 25 of the body 11 is a solenoid 23 including a solenoid plunger (actuator) 24. The plunger 24 is movable from a first position (shown in FIG. 1) to a second position (shown in FIG. 2) upon the solenoid 23 being electrically energised.

Figure 2:
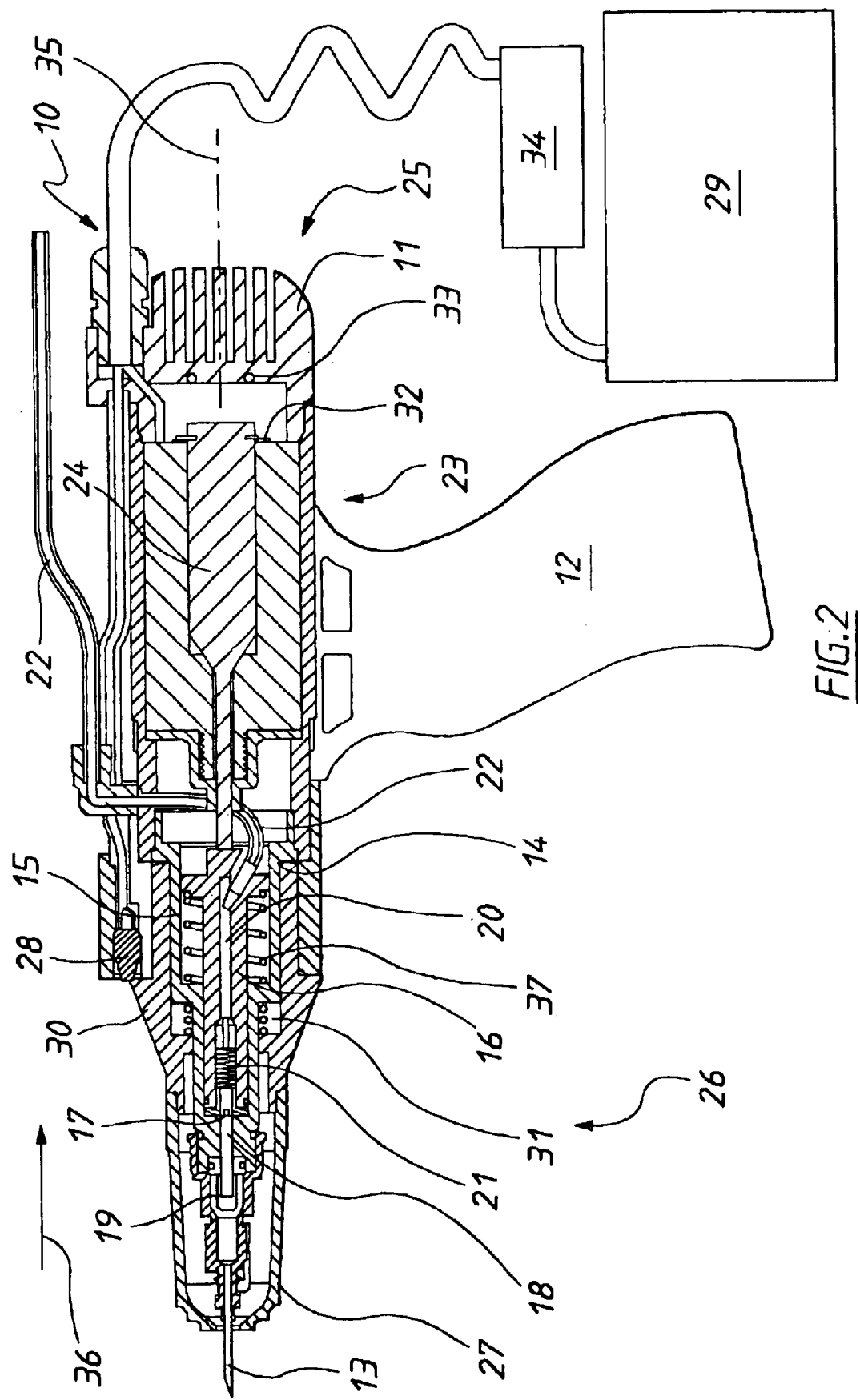
FIG. 2 is a schematic parts section side elevation of the injector of FIG. 1 in an activated condition.

The forward portion 26 of the plunger 24 is coupled to the piston 16 so that upon the solenoid 23 being energised the piston 16 is moved from the position shown in FIG. 1 to the position shown in FIG. 2, that is upon the solenoid 23 being energised the volume of the chamber 17 is reduced. When the solenoid 23 is de-energised the spring 37 returns the piston 16 and plunger 24 to the position shown in FIG. 1.

Mounted on the forward portion 26 of the body 11 is a needle shroud 27. The needle shroud 27 is movable from all extended position (FIG. 1) covering the needle 13, to a retracted position (FIG. 2) exposing the needle 13 for injection purposes More particularly, when the injector 10 is applied against the skin of an animal, the shroud 27 is caused to move in the direction of the arrow 36 so that the needle 13 penetrates the skill.

Mounted on the body 11 is an electric switch 28 electrically connecting a battery 29 with the solenoid 23. More particularly, the switch 28 is operated, the solenoid 23 is electrically activated. The switch 28 is engaged by a projection 30 of the shroud 27 when the shroud 27 is in the retracted position. Accordingly, upon the needle 13 penetrating to a desired depth, the shroud 27 engages the switch 28 and causes the solenoid 23 to be energised and the liquid to be injected.

The shroud 27 is urged by means of spring 31 from the retracted position (FIG. 2) to the extended position (FIG. 1). Accordingly, upon the needle 13 being withdrawn the shroud 27 returns to the position shown in FIG. 1 and releases the switch 25. Upon the switch 28 being released the solenoid 23 is de-energised. Accordingly, the piston 16 returns to the position shown in FIG. 1, drawing fresh liquid into the chamber 17.

The forward travel of the actuator 24 is determined by stop flanges 32, while provided in the body 11 is a resilient 'O-ring' 33 that cushions engagement of the actuator 24 with the body 11.

Interposed between the solenoid 23 and battery 29 is a relay assembly 34. More particularly the switch 28 operates the relay assembly 34 to connect the battery 29 to the solenoid 23.

In operation of the above-described injector 10, a user nicely grips the handle 12 and applies the injector 10 to the skin of the animal. Continued pressure will cause the shroud 27 to retract and the needle 13 to penetrate. When the shroud 27 is retracted to a position activating the switch 28, electric power is delivered to the solenoid 23 causing the actuator 24 to move the piston 16 to reduce the volume of the chamber 17. As the volume of the chamber 17 reduces liquid is delivered through the valve 19 and injected via the needle 13. Upon the user removing the injector 10 from the animal the shroud 7 moves to a position covering the needle 13 and releases the switch 28. When the switch 28 is released the relay assembly 34 electrically isolates the solenoid 23. Under the influence of the spring 37 the piston 16 moves to increase the volume of the chamber 17 and draws more liquid into the chamber 17.

The actuator 24 is directly coupled to the piston 16 so that both are caused to reciprocate linearly in unison along the longitudinal axis 35 of the injector 10.

What is claimed is:

1. A powered injector to deliver a liquid, said injector including:

a body;

a cylinder in the body;

a piston slidably mounted within the cylinder so as to cooperate therewith to enclose a variable volume chamber;

an outlet extending from said chamber and being adapted to receive a needle through which the liquid is delivered;

a needle shroud movably mounted on the body so as to be movable between an extended position at which the needle would be covered by the shroud, and a retracted position at which the needle is exposed;

an inlet extending to said chamber to deliver liquid thereto;

a solenoid mounted in the body and having a movable actuator connected to the piston, said actuator being caused to move generally linearly from a first position to a second position upon the solenoid being electrically energised, with said piston being caused to reduce the volume of said chamber when said actuator moves from said first position to said second position;

an electric switch connected to said solenoid to deliver electric power thereto to energise said solenoid, the switch being mounted on said body so as to be engaged by said shroud when moved to the retracted position thereof; and wherein when said shroud moves to said extended position said electric switch disconnects said solenoid from electric power so that said actuator moves from said second position to said first position causing said piston to increase the volume of said chamber and draw liquid into said chamber via said inlet.

2. The injector of claim 1 wherein said injector includes a spring urging said piston to increase the volume of said chamber.

3. The injector of claim 1 wherein the injector includes a one-way valve in said inlet restricting fluid to flow toward said chamber, and a valve in said outlet restricting fluid to flow toward said needle.

4. The injector of claims 1, 2 or 3 wherein said inlet includes a passage extending through said piston and a flexible conduit extending to said passage.

5. The injector of claim 1 wherein a spring urges said shroud to said extended position.

6. The injector of claim 1 wherein the injector includes a battery connected to said switch to deliver electric power to energize said solenoid.

7. The injector of claim 1, wherein said injector includes a spring urging said piston to increase the volume of said chamber and a one-way valve in said inlet restricting fluid to flow toward said chamber, and a valve in said outlet restricting fluid to flow toward said needle;

wherein said inlet includes a passage extending through said piston and a flexible conduit extending to said passage; wherein a spring urges said shroud to said extended position and wherein the injector includes a battery connected to said switch to deliver electric power to energise said solenoid.

* * * * *